(12) United States Patent
Calello et al.

(10) Patent No.: US 6,485,731 B2
(45) Date of Patent: Nov. 26, 2002

(54) METHOD FOR IMPROVING INTEGRITY OF COSMETIC FILMS

(75) Inventors: Joseph Frank Calello, Bridgewater, NJ (US); Amy Lynn Olsen, Edison, NJ (US); Richard P. Rosen, Princeton, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 19 days.

(21) Appl. No.: 09/755,250

(22) Filed: Jan. 8, 2001

(65) Prior Publication Data

US 2002/0136745 A1 Sep. 26, 2002

(51) Int. Cl.[7] .............................. A61K 6/00; A61K 7/00; A61K 7/04
(52) U.S. Cl. .......................................... 424/401; 424/61
(58) Field of Search ..................... 424/401, 61

(56) References Cited

U.S. PATENT DOCUMENTS

| | | | | |
|---|---|---|---|---|
| 3,632,744 A | * | 1/1972 | Paulsen | 424/69 |
| 5,312,968 A | | 5/1994 | O'Lenick | 560/182 |
| 5,358,719 A | * | 10/1994 | Mellul et al. | 424/497 |
| 5,446,114 A | | 8/1995 | O'Lenick | 528/15 |
| 5,473,038 A | | 12/1995 | O'Lenick | 528/15 |
| 6,251,375 B1 | * | 6/2001 | Bara | 424/61 |

FOREIGN PATENT DOCUMENTS

WO  WO 00/66073  11/2000

* cited by examiner

Primary Examiner—Thurman K. Page
Assistant Examiner—S. Howard
(74) Attorney, Agent, or Firm—Julie Blackburn

(57) ABSTRACT

A method for improving the integrity of a cosmetic film applied to nails or surrounding cuticle surfaces comprising applying to the surface an effective amount of a composition comprising less than 5% by weight of the total composition of a fluorinated oil. The invention also comprises a nail and cuticle conditioning composition and a semi-permanent film forming composition containing the fluorinated oil.

14 Claims, No Drawings

METHOD FOR IMPROVING INTEGRITY OF COSMETIC FILMS

TECHNICAL FIELD

The invention is in the field of cosmetic compositions for application to nails and surrounding cuticle tissue.

BACKGROUND OF THE INVENTION

The application of cosmetic and personal care products to the skin almost always involves the formation of a film on the skin. For example, application of a foundation to the face involves formation of a colored film on the skin. The same is true of products such as lipstick, eyeshadow, blush, nail enamel, and nail treatment products. The product is applied to the appropriate keratinous surface and allowed to dry. A film is formed which adheres to the skin for the appropriate period of time before being removed by chemical processes, or washed off with water.

The attributes of a cosmetic film depend on the type of product that is being formulated. Still, no matter what type of cosmetic is being prepared, the film integrity is of importance. Film integrity plays a direct role in the wear, appearance, and durability of the cosmetic.

Accordingly, there is a need for methods and ingredients that will enhance the integrity of a cosmetic film that is formed upon a keratinous surface. Film integrity is particularly important for products that are applied to the fingernails or toenails and surrounding cuticle tissue because these extremities are exposed to a wide variety of environmental assaults such as abrasion, detergents, bumping, and so on. Accordingly, cosmetic films applied to nails and surrounding tissue should advantageously have excellent moisture barrier properties, be capable of forming a cohesive film on the area that exhibits improved resistance to typical environmental assaults, and in addition be aesthetically pleasing.

Unexpectedly, it has been discovered that formulating compositions applied to nails and surrounding cuticle tissue with less than 5%, more preferably less than 1% by weight of a fluorinated oil will provide compositions that exhibit substantially improved films.

SUMMARY OF THE INVENTION

The invention comprises a method for improving the integrity of a cosmetic film formed on fingernails, toenails, and surrounding cuticular tissue comprising applying to said surfaces a composition containing less than 5% by weight of a fluorinated oil.

The invention also comprises a nail and cuticle conditioning composition comprising 0.00001 to 5% of a fluorinated oil, and 10–99% of a non-fluorinated oil.

The invention also comprises a semi-permanent film forming composition comprising 0.00001–5% of a fluorinated oil, 5–99% solvent and 1–85% of a film forming polymer.

The fluorinated oil will improve the film integrity in a variety of ways. First, due to its water repellant nature, the fluorinated oil in the composition will cause the composition to exhibit improved moisture barrier properties when applied to the desired surface due to phase separation. In particular, the fluorinated oil separates from the core composition and acts as improved barrier. This in turn may cause improvement in conditions such as dryness, cracking, and other undesirable characteristics of the nails and surrounding cuticle tissue. Often these types of conditions are exacerbated by exposure of the hands to detergents, water, and other environmental assaults. In addition, the presence of a fluorinated oil in semi-permanent film forming compositions such as nail enamel, will improve the integrity of the film by causing the film formed to exhibit improved gloss, leveling, and mar resistance in addition to water repellency. The improved gloss is due to the fluorinated oil migrating to the surface of the film formed on the nail after the nail enamel is applied to the nail and dried, e.g. phase separation. The solvents evaporate in the drying process, leaving the fluorinated oil on the surface of the dried film. The resulting finish exhibits improved gloss, improved water repellency, and the superficial fluorinated oil layer improves mar resistance. The term "mar resistance" means that the dried film is not as readily scratched or scuffed. In addition, the improved leveling provided by the fluorinated oil enables the nail enamel film to be evenly applied without bubbles or other surface aberrations, which irregularities also impair the integrity of the film. A film that maintains its integrity is better able to protect the surface to which it is applied. The amount of the fluorinated oil is critical in achieving the desired phase separation. In particular, if the amount of fluorinated oil is too great there will be little or no phase separation and the compositions will not exhibit the desired properties. If the amount of fluorinated oil is too small, not enough of the oil is present to exhibit the desired properties.

The amount of fluorinated oil contained within the composition is within a very narrow range. In particular, if the fluorinated oil is present at more than 5% by weight, the resulting compositions may be unstable and may separate with time, and will not provide the benefits described herein. The compositions used in the method of the invention may be oil based compositions for conditioning nails and surrounding tissue, or they may be semi-permanent film forming compositions in the form of pigmented nail enamel, basecoats, or topcoats. While both types of compositions are capable of forming a film on the nails and surrounding tissue to which they are applied, the nail enamel type compositions form what is referred to as a "semi-permanent" film in that the film cannot be removed by soap and water alone, but requires removal by organic solvent based removers. The term "film" when used in accordance with the invention means the film formed by conditioning compositions such as lotions, creams and the like which may be removed by soap and water, as well as the semi-permanent films formed by nail enamel compositions such as basecoats, topcoats, and color nail enamel products that require removal by organic solvent compositions.

DETAILED DESCRIPTION

The invention comprises a method for improving the integrity of a cosmetic film applied to nails or surrounding cuticle surfaces comprising applying to the surface an effective amount of a composition comprising less than about 5% by weight of the total composition of a fluorinated oil. (All percentages mentioned herein are percentages by weight unless otherwise indicated.)

The invention also comprises a nail and cuticle conditioning composition comprising 0.00001 to 5% of a fluorinated oil, and 10–99% of a non-fluorinated oil.

The invention also comprises a semi-permanent film forming composition comprising 0.00001–5% of a fluorinated oil, 5–99% solvent and 1–85% of a film forming polymer.

I. The Method of the Invention

Any type of composition normally applied to skin or surrounding cuticle tissue may be suitable for use in the claimed method so long as that composition is a suitable vehicle for the fluorinated oil and requisite amounts of the fluorinated oil is stable therein. Examples of such compositions include nail and cuticle treatment creams, lotions, and the like as well as nail enamel compositions including basecoats, topcoats, nail strengtheners, and regular pigmented nail enamel. The integrity of the film formed is improved in moisture barrier properties, and in the case of semi-permanent films, those films exhibit improved gloss, mar resistance, and water repellency as well.

The compositions containing the fluorinated oil may be applied to the nails or cuticle tissue one or more times per day. In the case where the composition is a cuticle or nail conditioning cream or lotion, the composition may be applied as often as desired. In the case where the composition is a nail enamel composition, the composition may be applied one or more times per day or as often as instructed by the product manufacturer.

The fluorinated oil used in the method of the invention may be an organic oil or a silicone oil.

The composition used in the method contains less than 5% by weight of the fluorinated oil. Including more than 5% by weight may cause the composition to be unstable and prone to separation, which comprises the commercial value of the compositions. Preferably the amount of fluorinated oil ranges from 0.0001 to 5, preferably 0.0005 to 3, more preferably 0.0005 to 1, more preferably 0.001 to 0.5%, most preferably from 0.001–0.05% by weight of the total composition. The fluorinated oil may be an organic oil or a silicone oil. The term "fluorinated oil" means an ingredient that is a liquid, semi-solid, or solid (e.g. having a wax-like consistency) at room temperature and has one or more fluorine substitutions in the molecular structure. Preferably, the fluorinated oil is a liquid or semi-solid at room temperature and has a viscosity of 5 to 500,000, more preferably 10 to 250,000 centipoise, most preferably 20 to 200,000 centipoise at 25° C.

Suitable fluorinated oils include silicones, esters, or perfluoropolyethers.

A. Fluorinated Silicone Oils

Suitable fluorinated silicone oils include trimethylsilyl endcapped fluorosilicone oils, polytrifluoropropylmethylsiloxanes, and similar silicones. Such silicones may be linear or cyclic, and will contain one or more fluorine atoms substituted for the hydrogen atoms on the carbon atom. Preferably the fluorinated silicone is a water insoluble nonvolatile silicone. The term "nonvolatile" means that the silicone has a vapor pressure of less than 2 mm. of mercury at 20° C.

One type of fluorinated silicone that may be used in the method of the invention is disclosed in U.S. Pat. No. 5,473,038 which is hereby incorporated by reference in its entirety. Such silicones have the general formula:

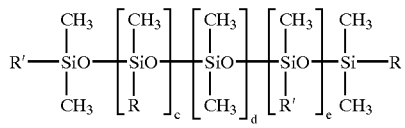

wherein:
R' is —$(CH_2)_a$—$CH_3$
R is $C_{1-4}$ alkyl, —$(CH_2)_a$—$(CF_2)_b CF_3$
a is 0 to 100
b is 0 to 100
c is 0 to 100
d is 0 to 100
e is 0 to 100, with the proviso that the polymer must contain at least one fluorine substituted moiety.

Preferred are fluorinated silicones of the above formula wherein R' and R are $C_{1-4}$ alkyl, c is 1–100, d is 1–100, e is 0, and R is —$(CH_2)_a$—$(CF_2)_b CF_3$ wherein a is 1–12 and b is 0 to 10.

Particularly preferred are the fluorinated silicones trifluoromethyl $C_{1-4}$ alkyl dimethicone and fluoro $C_{2-8}$ alkyl dimethicone.

Another fluorosilicone suitable for use in the method comprises fluorinated dimethicone copolyols as disclosed in U.S. Pat. No. 5,446,114, which is hereby incorporated by reference. Such compounds have the general formula:

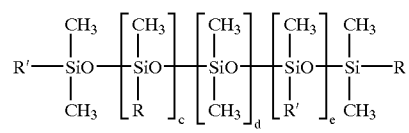

wherein:
R' is $C_{1-4}$ alkyl, or —$(CH_2)_3$—O—$(EO)_a$—$(PO)_b$—$(EO)_c$—H
R is $C_{1-4}$ alkyl, —$(CH_2)_a$—$(CF_2)_b CF_3$
EO is —$(CH_2 CH_2$—O)—
PO is —$(CH_2 CH(CH_3)$—O)—
a is 0 to 100
b is 0 to 100
c is 0 to 100
d is 0 to 100
e is 0 to 100, with the proviso that the polymer must contain at least one fluorine substituted radical and at least one alkylene oxide moiety.

Also suitable as the fluorinated silicone are fluorine containing silicone polyester compounds as disclosed in U.S. Pat. No. 5,235,017 which is hereby incorporated by reference in its entirety. Such compounds are formed by the esterification of a dimethicone copolyol having the general formula:

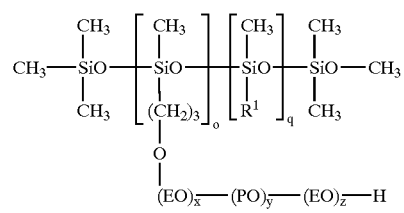

wherein
o is 1 to 20
q is 1 to 20
EO is —$(CH_2$—$CH_2$—O—)—
PO is —(—$CH_2$—$CH(CH_3)$—O—)—; and
x, y, and z are integers ranging from 0 to 20 with a diacid selected from the group:
HO(O)C—$(CH_2)_c$—C(O)OH; HO(O)C—$(CH_2)_d$—CH=CH—$(CH_2)_e$—C(O)OH and dimer acids, wherein c, d, and e are independently integers from 1 to 10; and a fluorine containing hydroxy compound having the following formula:

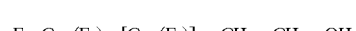

wherein n ranges from 3 to 17.

One example of a such a compound is dimethiconol fluoroalcohol dilinoleic acid.

Other types of fluorinated silicone that may be used in the claimed method are silicone fluoroesters as disclosed in U.S. Pat. No. 6,008,397 which is hereby incorporated by reference in its entirety. These silicones are made by reacting a carboxy silicone and a fluoroalcohol.

B. Fluorinated Organic Oils

Also suitable for use in the claimed method are various types of fluorinated organic oils such as esters, perfluoropolyethers, and so on.

1. Esters

Fluorine containing citrate esters are particularly suitable for use in the claimed method. Such esters are disclosed in U.S. Pat. No. 5,312,968, which is hereby incorporated by reference. Further examples of such esters include those of the general formula:

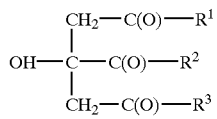

wherein $R^1$, $R^2$, and $R^3$ are each independently an alkyl having 4 to 30 carbon atoms, or

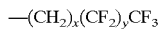

where x is 0–10, and y is 1–20; with the proviso that at least one of $R^1$, $R^2$ and $R^3$ is —$(CH_2)_x(CF_2)_yCF_3$ Preferred is the above compound wherein $R^1$ and $R^2$ are 4–20 alkyl and $R^3$ is —$(CH_2)_x(CF_2)_yCF_3$. Particularly preferred is wherein R' and $R^2$ are octyldodecyl and $R^3$ is —$(CH_2)_x(CF_2)_yCF_3$ wherein x is 2 and y is 4. This compound has the CTFA name dioctyldodecyl fluoroheptyl citrate.

Also suitable are fluorinated meadowfoam esters which are prepared by the esterification of meadowfoam oil with one or more fluorinated alcohols using the same synthetic methods taught in U.S. Pat. No. 5,786,388, which is hereby incorporated by reference. In particular, this patent teaches the synthesis of meadowfoam esters by esterification of the fatty acids found in meadowfoam oil with one or more alcohols. Such alcohols may be regular fatty alcohols or fluorinated alcohols. Particularly preferred is a fluorinated meadowfoam ester having the CTFA name fluoro octyldodecyl meadowfoamate.

2. Perfluoropolyethers

Also suitable are perfluoropolyethers like those disclosed in U.S. Pat. Nos. 5,183,589, 4,803,067, and 5,183,588, all of which are incorporated by reference, are also suitable. These perfluoropolyethers are commercially available from Montefluos under the tradename Fomblin.

The fluorinated oils may be used in one or more compositions designed to be applied to nails or surrounding cuticle tissue, as more fully described below.

II. The Compositions Used in the Method

The compositions used in the method of the invention may be conditioning compositions which provide a film on the keratinous surface that is removed by soap and water washing, or the film may be semi-permanent which means that it is not removed without use of chemicals such as organic solvents. Examples of both types of compositions include cuticle moisturizers and conditioners, nail strengthening conditioners, nail enamel basecoat or topcoat composition, or regular pigmented nail enamel. The compositions may contain water or may be anhydrous. Preferably the compositions are substantially anhydrous which means that they contain less than 5% by weight of water, more preferably less than 3%, most preferably less than 1% by weight of water. Although the preferred compositions are substantially anhydrous, a wide variety of compositions suitable for use in the invention may contain appreciable amounts of water such as waterborne nail enamel, cuticle creams and lotions, etc.

A. Conditioning and Moisturizing Compositions

A variety of conditioning and moisturizing compositions containing the fluorinated oil may be used in the method of the invention. Such compositions may contain oils, structuring agents such as waxes, extracts, nutrients, preservatives, and so on.

1. Oils

A wide variety of non-fluorinated oils may be used in the compositions. Generally such compositions contain about 10–99%, preferably 15–90%, more preferably 20–85% by weight of the total composition of one or more oils. Suitable oils include silicone oils and organic oils which may be volatile or nonvolatile.

(a) Volatile Oils

The oils used may be volatile or nonvolatile. The term "volatile" means that the oil has a measureable vapor pressure, or a vapor pressure of at least 2 mm. of mercury at 20° C. The term "nonvolatile" means that the oil has a vapor pressure of less than 2 mm. of mercury at 20° C. Suitable volatile solvents generally have a viscosity of 0.5 to 10 centistokes at 25° C. Suitable volatile oils include linear silicones, cyclic silicones, paraffinic hydrocarbons, or mixtures thereof.

Cyclic silicones (or cyclomethicones) are of the general formula:

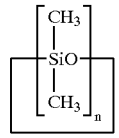

where n=3–6.

Linear volatile silicones in accordance with the invention have the general formula:

where n=0–7, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

Also suitable as the volatile oils are various straight or branched chain paraffinic hydrocarbons having 5 to 40 carbon atoms, more preferably 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70–225, preferably 160 to 190 and a boiling point range of 30 to 320, preferably 60–260 degrees C., and a viscosity of less than 10 cs. at 25 degrees C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename Permethyl 99A. Various $C_{16}$ isoparaffins commercially available, such as isohexadecane (having the tradename Permethyl R), are also suitable. Transfer resistant cosmetic sticks of the invention will generally comprise a mixture of volatile silicones and volatile paraffinic hydrocarbons.

(b) Nonvolatile Oils

A variety of nonvolatile oils are also suitable for use in the cosmetic compositions of the invention. The nonvolatile oils generally have a viscosity of greater than 10 centipoise at 25° C., and may range in viscosity up to 1,000,000 centipoise at 25° C. Examples of nonvolatile oils suitable for use in the cosmetic sticks of the invention include esters of the formula RCO—OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like, as well as the esters disclosed on pages 24–26 of the C.T.F.A. Cosmetic Ingredient Handbook, First Edition, 1988, which is hereby incorporated by reference.

The oil may also comprise naturally occuring glyceryl esters of fatty acids, or triglycerides. Both vegetable and animal sources may be used. Examples of such oils include castor oil, lanolin oil, triisocetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable as the oil are synthetic or semi-synthetic glyceryl esters, e.g. fatty acid mono-, di-, and triglycerides which are natural fats or oils that have been modified, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as the oil are nonvolatile hydrocarbons such as isoparaffins, hydrogenated polyisobutene, mineral oil, squalene, petrolatum, and so on.

Straight or branched chain fatty alcohols having the formula R—OH, wherein R is a straight or branched chain saturated or unsaturated alkyl having 6–30 carbon atoms, are also suitable oils. Such fatty alcohols include cetyl alcohol, stearyl alcohol, cetearyl alcohol, and the like.

Also suitable as the oil are various lanolin derivatives such as acetylated lanolin, acetylated lanolin alcohol, and so on.

Nonvolatile silicones, both water soluble and water insoluble, are also suitable as the oil component. Such silicones preferably have a viscosity of 10 to 600,000 centistokes, preferably 20 to 100,000 centistokes at 25° C. Suitable water insoluble silicones include amodimethicone, bisphenylhexamethicone, dimethicone, hexadecyl methicone, methicone, phenyl trimethicone, simethicone, dimethylhydrogensiloxane, stearoxytrimethylsilane, vinyldimethicone, and mixtures thereof. Also suitable are water soluble silicones such as dimethicone copolyol, dimethiconol, and the like. Such silicones are available from Dow Corning as the 3225C formulation aid, Dow 190 and 193 fluids, or similar products marketed by Goldschmidt under the ABIL tradename.

Guerbet esters are also suitable oils. The term "guerbet ester" means an ester which is formed by the reaction of a guerbet alcohol having the general formula:

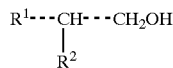

with a carboxylic acid having the general formula:

or

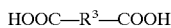

wherein $R^1$ and $R^2$ are each independently a $C_{4-20}$ alkyl and $R^3$ is a substituted or unsubstituted fatty radical such as a $C_{1-50}$ straight or branched chain saturated or unsaturated alkyl or alkylene, or phenyl, wherein the substituents are halogen, hydroxyl, carboxyl, and alkylcarbonylhydroxy. Particularly preferred is a carboxylic acid wherein the R group is such to provide an ingredient known as meadowfoam seed oil.

2. Vitamins and Antioxidants

The compositions used in the method of the invention may contain vitamins and/or coenzymes, as well as antioxidants. If so, 0.0001–10%, preferably 0.0005–8%, more preferably 0.001–5% by weight of the total composition are suggested. Suitable vitamins include the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof In addition, Vitamins D, K, and C are also suitable.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

3. Preservatives

The composition may contain 0.0001–8%, preferably 0.001–6%, more preferably 0.005–5% by weight of the total composition of preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, calcium benzoate, calcium propionate, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and all of those disclosed on pages 570 to 571 of the CTFA Cosmetic Ingredient Handbook, Second Edition, 1992, which is hereby incorporated by reference.

4. Waxes

The compositions used in the method of the invention may, if desired, contain one or more waxes. If present, suggested ranges are from about 1–70%, preferably 1–30%, more preferably 1–25% by weight of a cosmetically acceptable natural or synthetic wax. The waxes that can be used are solid or semi-solid waxes having a melting point of 30 to 120° C. and generally includes animal waxes, plant waxes, mineral waxes, silicone waxes, synthetic waxes, and petroleum waxes.

Examples of waxes in accordance with the invention include bayberry, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, ozokerite, paraffin, PEG-6 beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, synthetic wax, stearoxy dimethicone, dimethicone behenate, stearyl dimethicone, and the like, as well synthetic homo- and copolymer waxes from the ethylene series. In the preferred embodiment of the invention the waxes are polymers of ethylene and/or propylene.

5. Plant Extracts

It may also be desireable to add various types of plant extracts. If so, 0.0001–5%, preferably 0.001–4%, more preferably 0.01–2% is suggested. Suitable plant extracts include intact and hydrolyzed extensins such as those set forth in U.S. Pat. No. 5,443,855, which is hereby incorporated by reference. Also suitable are extracts of acacia extract, algae, alfalfa, aloe, aloe barbadensis, gingko, bayberry, avocado, calendula, broom, apple, anise, birch, bitter orange, as well as those set forth on pages 493–494 of the CTFA Cosmetic Ingredient Handbook, Second Edition, 1992, which is hereby incorporated by reference. Particularly preferred is aloe barbadensis extract.

The conditioning compositions are applied to nails or cuticles and provide moisturization and conditioning to nail and cuticle tissue.

B. Semi-Permanent Film Forming Compositions

Suitable for use in practice of the claimed method are film forming compositions that provide a semi-permanent film removable with organic solvents, such as nail enamel.

1. Solvents

Suitable solvents that may be used in nail coating compositions are organic solvents or water. Preferably, the composition contains 5–99%, preferably 10–95%, more preferably 15–85% by weight of the total composition of solvent. The solvent may be aqueous or non-aqueous or a mixture of both types of solvents. Suitable non-aqueous solvents include aliphatic or aromatic ketones such as acetone, diacetone alcohol, dihydroxyacetone, ethyl butyl valerolactone, methyl ethyl ketone, and the like; aliphatic or aromatic alcohols such as methanol, propanol, benzyl alcohol, butoxyethanol, butoxypropanol, butyl alcohol, 3-methyl-3-methoxy-butanol, t-butyl alcohol, butylene glycol, diethylene glycol, abietyl alcohol, propylene carbonate, hexyl alcohol, isopropanol, and the like; glycol ethers; esters such as butyl acetate, ethyl acetate, etc.

2. Film Forming Polymer

Semi-permanent compositions generally comprise one or more film forming polymers that form a semi-permanent film on the keratinous surface.

A wide variety of film forming polymers may be used in the cosmetic or personal care products of the invention. The film forming polymer must be capable of forming a film on the skin, nails, or hair. The film forming polymers may be natural or synthetic, or a combination of both, and may be in the form of solids, semi-solids, or liquids. The film forming polymer may be neutral or ionic in character, e.g. anionic, cationic, nonionic, or amphoteric. Suggested ranges of film forming polymer are 1–85%, preferably 2–80%, more preferably 5–70% by weight of the total composition.

(a). Synthetic Polymers

Suitable synthetic polymers include homopolymers, copolymers, and block and graft copolymers comprised of repeating monomers such as acrylic or methacrylic acid or esters thereof, urethanes, esters, amides, styrene, vinyl, silicon, and so on. The synthetic polymers may be present in the composition in ranges from 0.1–95%, preferably 1–85%, more preferably 3–45% by weight of the total composition.

Examples of synthetic film forming polymers include those set forth in the CTFA Cosmetic Ingredient Dictionary and Handbook, Eighth Edition, 2000, pages 1744 through 1747, which are hereby incorporated by reference, including those which are summarized herein.

(i) Silicone Resins

Cross-linked silicones, also known as silicone resins, can be plasticized with $C_{1-20}$ esters of malic acid, and are suitable for use in the compositions and method of the invention. Preferred silicone resins have the general formula:

wherein R, R' and R" are each independently a $C_{1-10}$ straight or branched chain alkyl or phenyl, and x and y are such that the ratio of $(RR'R")_3SiO_{1/2}$ units to $SiO_2$ units is 0.5 to 1 to 1.5 to 1.

Preferably R, R' and R" are a $C_{1-6}$ alkyl, and more preferably are methyl and x and y are such that the ratio of $(CH_3)_3SiO_{1/2}$ units to $SiO_2$ units is 0.75 to 1. Most preferred is this trimethylsiloxy silicate containing 2.4 to 2.9 weight percent hydroxyl groups which is formed by the reaction of the sodium salt of silicic acid, chlorotrimethylsilane, and isopropyl alcohol. The manufacture of trimethylsiloxy silicate is set forth in U.S. Pat. Nos. 2,676,182; 3,541,205; and 3,836,437, all of which are hereby incorporated by reference. Trimethylsiloxy silicate as described is available from Dow Corning Corporation under the tradename 2-0749 and 2-0747, which is a blend of about 40–60% volatile silicone and 40–60% trimethylsiloxy silicate. Dow Corning 2-0749 in particular, is a fluid containing about 50% trimethylsiloxy silicate and about 50% cyclomethicone. The fluid has a viscosity of 200–700 centipoise at 25° C., a specific gravity of 1.00 to 1.10 at 25° C., and a refractive index of 1.40–1.41.

(ii). Copolymers of Silicone and Organic Monomers

Also suitable for use as the film forming polymer in the compositions and method of the invention are copolymers of silicone and various organic, ethylenically unsaturated monomers, and optionally other monomers. Examples of such polymers are disclosed in U.S. Pat. No. 6,033,650, which is hereby incorporated by reference. Preferred examples of these polymers include graft or block copolymers comprised of silicon moieties and C1-12 alkyl acrylate or methacrylate monomers which may be substituted with one or more groups such as halogen or hydroxy, also referred to as silicone/acrylate copolymers. Suitable silicone acrylate copolymers may be purchased from 3M Company under the tradenames VS-70 and SA-70, or from Shin Etsu Silicones.

(iii). Urethane Homo- and Copolymers

Also suitable for use in the compositions and method of the invention are homo and copolymers of urethane.

Homopolymers of urethane are often sold in an aqueous dispersion from vendors such as Alloid Colloids, B. F. Goodrich, and the like. Suitable urethane copolymers may be comprised of urethane monomers copolymerized with organic compounds, or other synthetic monomers.

(iv). Amides and Amines

Also suitable are various synthetic polymers containing amide or amine substituent groups. Examples of such polymers include nylon, ammonium polyacrylate, acrylamides copolymer, acrylates/acrylamide copolymers, acrylates ammonium acrylate copolymer, acrylates C10-20 alkyl acrylate cross polymer, acrylates/carbamate crosspolymer, acrylates ceteth-20 itaconate copolymer, acrylates/ dimethylaminoethyl methacrylate copolymer, ammonium acrylates copolymer, ammonium polyacrylate, ammonium styrene/acrylates copolymer, ammonium vinyl acetate/ acrylates copolymer, aminomethylpropanol/acrylates/ dimethylaminoethylmethacrylate copolymer, and so on.

(v). Other Synthetic Polymers

Preferred are synthetic polymers are comprised of one or more monomers selected from the following general formula:

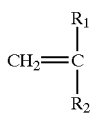

wherein $R_1$ is H, a $C_{1-30}$ straight or branched chain alkyl, aryl, aralkyl; $R_2$ is a pyrrolidone, or a substituted or unsubstituted aromatic, alicyclic, or bicyclic ring where the substitutents are $C_{1-30}$ straight or branched chain alkyl, or COOM wherein M is H, a $C_{1-30}$ straight or branched chain alkyl, pyrrolidone, or a substituted or unsubstituted aromatic, alicylic, or bicyclic ring where the substitutents are $C_{1-30}$ straight or branched chain alkyl which may be substituted with one or more halogens.

Even more preferred as synthetic polymers which comprise polar monomers such as acrylic acid or methacrylic acid, in combination with $C_{1-6}$ esters thereof. Most preferred is a synthetic polymer which comprises monomers of butyl methacrylate and acrylic acid.

(b). Natural Polymers

A variety of natural polymers, or derivatives thereof are suitable, including cellulosics, chitins, chitosans, shellac, rosins, resins, animal or vegetable proteins and polypeptides, and so on. The natural polymers may be present in ranges from 0.1–95%, preferably 1–85%, more preferably 3–45% by weight of the total composition.

(i). Cellulosics

Examples of suitable cellulosic polymers include nitrocellulose, mono- or diesters of cellulose formed by the reaction of cellulose with various organic acids, for example straight or branched chain carboxylic acids having from one to twenty, preferably one to ten carbon atoms, which may be substitued with one or more hydroxyl groups, Examples of such cellulosics include cellulose acetate, cellulose acetate isobutyrate, cellulose acetate propionate, cellulose acetate propionate carboxylate. Also suitable are cellulose polymers prepared by reacting with groups such as hydroxyl, alkoxyalkyl, hydroxylalkyl where the alkoxyalkyl and alkyl groups have from about one to ten carbon atoms. Examples of such polymers are carboxylmethyl hydroxyethylcellulose, carboxymethylcellulose, ethyl cellulose, hydroxyethylcellulose, methyl ethylcellulose, hydroxypropylcellulose, hydroxylbutyl cellulose, hydroxybutyl methylcellulose, and so on.

(ii). Chitin or Chitosan

Chitins, or chitosan and derivatives thereof are also suitable natural film forming polymers for use in the compositions and method of the invention. Chitin is defined as a polysaccharide derived from the exoskeleton of marine invertebrates which contains chiefly N-acetyl-glucosamine residues. Chitosan is chitin that has been deacetylated. Both polymers may be used as is, or esterified to form mono-, di-, or triesters by reacting with various straight or branched chain organic acids having from one to thirty carbon atoms, alpha or beta hydroxy acids, or di- or tricarboxylic acids. Examples of chitin or chitosan esters include chitosan adipate, chitosan ascorbate, chitosan formate, chitosan glycolate, chitosan lactate, chitsan PCA, chitosan salicylate, chitosan succinamate, and so forth. Also suitable are simple derivatives of chitin or chitosan, which are formed by substituting moieties such as hydroxyl, $C_{1-6}$ alkoxy, and the like on the polymer. Examples of such derivatives include carboxylbutyl chitosan, carboxylmethyl chitosan, carboxyethyl chitosan, carboxylbutyl chitosan, and so on.

(iii). Proteins

Also suitable as film forming polymers are various animal and vegetable proteins including hydrolyzed animal protein, albumin, serum albumin, hydrolyzed wheat protein, hydrolyzed soy protein, hydrolyzed animal collagen, and mixtures thereof.

(iv). Dextrans

Also suitable are dextrans and alkoxy, or alkoxylalkyl derivatives thereof such as carboxymethyl dextran, carboxylethyl dextran, and so on.

(v). Rosins, Resins and Gums

Also suitable are various natural resins and rosins and derivatives thereof such as Balsam Canada resin, hydrogenated rosin, glycol rosinate, shellac, and the like. Various gums are also suitable including acacia gum, and similar materials.

It may be desirable to have more than one film forming polymer in the composition. They polymers may be a combination of one or more synthetic polymers, or one or more natural polymers, or mixtures of both.

The preferred semi-permanent film forming compositions of the invention comprise nitrocellulose.

3. Plasticizers

Preferably, the nail enamel compositions contain one more plasticizers that plasticize the film formed on the nail after the composition is applied to the nail and allowed to try. Suggested ranges of plasticizer are 0.1–35%, preferably 0.5–30%, more preferably 1–25% by weight of the total composition. Suitable plasticizers include glyceryl, glycol, and citrate esters as disclosed in U.S. Pat. No. 5,066,484, which is hereby incorporated by reference. Examples of such esters include glyceryl tribenzoate, glyceryl triacetate, acetyl tributyl citrate, dipropylene glycol dibenzoate, and the like. Also suitable, are plasticizers of the following general formula:

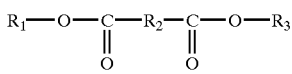

wherein $R_1$, $R_2$, and $R_3$ are each independently a $C_{1-20}$ straight or branched chain alkyl or alkylene which may be substituted with one or more hydroxyl groups. Preferably, $R_1$ is a $C_{3-10}$ straight or branched chain alkyl; $R_2$ is a $C_{2-8}$ alkyl which may be substituted with one or more hydroxyl groups; and $R_3$ is a $C_{3-10}$ straight or branched chain alkyl. Examples of such compounds include dioctyl malate, diisopropyl adipate, dibutyl sebacate, dioactyl azelate, dioctyl succinate, dioctyl fumarate, and the like

4. Pigments

The semi-permanent film forming compositions of the invention may be pigmented or clear. If pigmented, generally 0.1–30% by weight of the total composition, preferably 0.5–20%, more preferably 1–15% of pigment is suggested. Pigments suitable for use in nail enamel compositions are well known and include iron oxides, D&C and FD&C colors, titanium dioxide, and the like. The pigments may be treated or coated with agents which modify the surface properties such as silicones. Examples of silicone treated pigments which can be used in the compositions of the invention are set forth in U.S. Pat. No. 4,832,944, which is hereby incorporated by reference.

5. Suspending Agents

If the semi-permanent film forming compositions of the invention contain pigments, it is desirable to also incorporate 0.01–15%, preferably 0.05–10%, more preferably 0.1–8% by weight of the total composition of a suspending agent which acts to suspend the pigments in the formulation. Suitable suspending agents are montmorillonite minerals and derivatives thereof, such as stearalkonium bentonite, hectorites, attapulgite, bentones, and the like, as well as polymeric compounds known as associative thickeners. Suitable associative thickeners generally contain a hydrophilic backbone and hydrophobic side groups. Examples of such thickeners include polyacrylates with hydrophobic side groups, cellulose ethers with hydrophobic side groups, polyurethane thickeners. Examples of hydrophobic side groups are long chain alkyl groups such as dodecyl, hexadecyl, or octadecyl; alkylaryl groups such as octylphenyl or nonyphenyl.

7. Other Ingredients

The semi-permanent film forming compositions may contain a variety of other ingredients including vitamins, antioxidants, preservatives and plant extracts in the same ranges as set forth herein with respect to the conditioning compositions.

The semi-permanent film forming compositions used in the method exhibit improved moisture barrier properties due to the presence of the fluorinated oil. In addition, such compostions provide films that are substantially glossier and more resistant to chipping or marring.

The invention will be further described in connection with the following examples which are set forth for the purposes of illustration only.

EXAMPLE 1

A composition for protecting and strengthening nails was made according to the following formula:

|  | w/w % |
|---|---|
| Ethyl Acetate | 38.54 |
| Isopropyl alcohol | 35.79 |
| Nitrocellulose | 15.75 |
| Acetyl Tributyl citrate | 5.00 |
| Menthol | 0.75 |
| Panthenol | 1.00 |
| Dimethyl urea | 0.10 |
| Water | 0.50 |
| Tetrabutyl phenyl Hydroxybenzoate | 0.0001 |
| Methoxypropanol | 0.50 |
| 10% Calcium pantothenate solution | 0.02 |
| Trifluoromethyl C1–4 alkyl dimethicone | 0.05 |

-continued

|  | w/w % |
|---|---|
| Dioctyldodecyl fluoroheptyl Citrate, water, cyclomethicone | 0.001 |
| Retinyl palmitate | 0.001 |
| Tocopherol acetate | 0.001 |
| Aloe barbadensis extract | 0.001 |
| Ferric ammonium ferrocyanide and Violet #2 | QS |

The composition was made by combining all of the ingredients and mixing well. The composition was stored in a glass nail enamel bottle having a brush applicator appended to the cap.

EXAMPLE 2

An oil for conditioning and moisturizing the cuticle area was made as follows:

|  | w/w % |
|---|---|
| Octyl palmitate | 52.73 |
| Tridecyl trimellitate | 45.00 |
| Preservatives | 1.37 |
| Aloe barbadensis extract | 0.25 |
| Tocopheryl acetate | 0.25 |
| Sorbic acid | 0.20 |
| BHA | 0.15 |
| Perfluorononyl octyldodecyl glycol meadowfoamate | 0.05 |
| Retinyl palmitate | 0.001 |
| Ascorbyl palmitate | 0.0001 |
| Isopropyl myristate/D&C Violet #2/D&C Red #17 | QS |

The composition was made by adding the ingredients sequentially and mixing well. The composition was filled into a glass jar.

EXAMPLE 3

A nail enamel base and topcoat composition was prepared according to the following formula:

|  | w/w % |
|---|---|
| Ethyl acetate | 37.90 |
| Butyl acetate | 26.30 |
| ¼ sec. nitrocellulose | 13.30 |
| Tribenzoin | 10.33 |
| Isopropyl alcohol | 7.00 |
| Acetyl tributyl citrate | 3.50 |
| Triacetin | 0.90 |
| Water | 0.50 |
| Tetrabutyl phenyl hydroxybenzoate | 0.25 |
| Trifluoromethyl C1–4 alkyl dimethicone | 0.02 |
| Dioctyldodecyl fluoroheptyl citrate/water/cyclomethicone | 0.001 |
| Retinyl palmitate | 0.001 |
| Tocopherol acetate | 0.001 |
| Aloe barbadensis extract | 0.001 |
| D&C violet #2 | QS |

The composition was prepared by combining all the ingredients and mixing well. The mixture was stored in glass bottle nail enamel containers.

EXAMPLE 4

A nail enamel topcoat composition was prepared according to the following formula:

| | w/w % |
|---|---|
| Ethyl acetate | 40.12 |
| Butyl acetate | 24.40 |
| ½ sec. nitrocellulose | 7.06 |
| ¼ sec. nitrocellulose | 3.92 |
| Acrylates copolymer | 10.00 |
| Tribenzoin | 8.20 |
| Isopropyl alcohol | 4.70 |
| Triacetin | 1.00 |
| Etocrylene | 0.50 |
| Trifluoromethyl C1–4 alkyl dimethicone | 0.10 |
| Dioctyldodecyl fluoroheptyl citrate/water/cyclomethicone | 0.001 |
| Tocopherol acetate | 0.001 |
| Aloe barbadensis extract | 0.001 |
| Retinyl palmitate | 0.0001 |
| D&C Violet #2 | QS |

The composition was made by combining all of the ingredients and mixing well. The composition was stored in glass nail enamel containers.

EXAMPLE 5

A nail strengthening and conditioning composition was made according to the following formula:

| | w/w % |
|---|---|
| Ethyl acetate | 33.74 |
| Butyl acetate | 21.98 |
| ¼ sec. nitrocelluose | 17.64 |
| Tribenzoin | 12.80 |
| Isopropyl alcohol | 7.56 |
| Acetyl tributyl citrate | 4.65 |
| Triacetin | 1.27 |
| Tetrabutyl phenyl hydroxybenzoate | 0.24 |
| Dioctyldodecyl fluoroheptyl citrate/water/cyclomethicone | 0.05 |
| Trifluoromethyl C1–4 alkyl dimethicone | 0.05 |
| Retinyl palmitate | 0.001 |
| Tocopherol acetate | 0.001 |
| Aloe barbadensis extract | 0.001 |
| D&C Red #6 barium lake/D&C Red #7 calcium lake and D&C Yellow #11 | QS |

EXAMPLE 6

A cuticle conditioning and moisturizing composition was made according to the following formula:

| | w/w % |
|---|---|
| Trioctyldodecyl citrate | 44.00 |
| Isotridecyl isononanoate | 23.70 |
| C10–30 cholesterol/lanosterol ester | 9.50 |
| Mica | 9.50 |
| Synthetic wax | 6.70 |
| Paraffin wax | 2.80 |
| Cetyl alcohol | 2.30 |
| Quaternium-18 hectorite | 0.50 |
| Methylparaben | 0.30 |
| Sorbic acid | 0.20 |
| Aloe barbadensis extract | 0.10 |
| Tocopherol acetate | 0.10 |
| Perfluorononyl octyldodecyl glycol meadowfoamate | 0.10 |
| Propylparaben | 0.10 |
| BHA | 0.10 |
| Retinyl palmitate | 0.001 |
| FD&C Yellow #5 aluminum lake/D&C Red #7 calcium lake/titanium dioxide | QS |

The composition was prepared by sequentially combining all of the ingredients and mixing well. The composition was stored in a plastic jar with screw cap.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A method for improving the integrity of a cosmetic film applied to nails or surrounding cuticle surfaces comprising applying to the surface an effective amount of a composition comprising less than 5% by weight of the total composition of a fluorinated oil which phase separates from the composition after it is applied wherein the composition further comprises 10–97% by weight of a solvent and 0.5–35% by weight of a film forming polymer.

2. The method of claim 1 wherein the fluorinated oil is an organic oil having one or more fluorine substitutions in its molecular structure.

3. The method of claim 1 wherein the fluorinated oil is a silicone oil having one or more fluorine substitutions in its molecular structure.

4. The method of claim 1 wherein the fluorinated oil is a liquid at room temperature and has a viscosity of 5 to 500,000 centipoise at 25° C.

5. The method of claim 1 wherein the film is a semi-permanent film.

6. The method of claim 5 wherein the surface is a nail.

7. The method of claim 5 wherein the integrity of the film is enhanced by improving gloss, leveling, mar resistance, and water repellency.

8. The method of claim 1 wherein the solvent is selected from the group consisting of water, organic solvents, and mixtures thereof.

9. The method of claim 8 wherein the solvent is an organic solvent.

10. The method of claim 1 wherein the film forming polymer is a cellulose polymer or an acrylic polymer.

11. A semi-permanent film forming composition comprising 0.00001–5% of a fluorinated oil, 5–99% solvent and 1–85% of a film forming polymer wherein the fluorinated oil phase separates from the composition after application and improves the integrity of the film formed by the film forming polymer.

12. The composition of claim 11 which is a nail coating composition.

13. The composition of claim 11 wherein the solvent comprises an organic solvent.

14. The composition of claim 11 wherein the film forming polymer comprises a cellulosic polymer.

* * * * *